(12) United States Patent
Hegde et al.

(10) Patent No.: US 7,980,248 B2
(45) Date of Patent: Jul. 19, 2011

(54) DELIVERY TOOLS FOR SLEEP DISORDERS TREATMENT IMPLANT AND METHODS OF IMPLANTATION

(76) Inventors: Anant V. Hegde, Hayward, CA (US);
Kasey Kai-Chi Li, Palo Alto, CA (US);
Phil Houle, Sunnyvale, CA (US);
Casidy Hallsten, San Mateo, CA (US);
Chris D. Owen, Manteca, CA (US)

( * ) Notice: Subject to any disclaimer, the term of this patent is extended or adjusted under 35 U.S.C. 154(b) by 560 days.

(21) Appl. No.: 12/168,820

(22) Filed: Jul. 7, 2008

(65) Prior Publication Data

US 2010/0049227 A1    Feb. 25, 2010

Related U.S. Application Data

(63) Continuation-in-part of application No. 11/233,493, filed on Sep. 21, 2005, which is a continuation-in-part of application No. 10/946,435, filed on Sep. 21, 2005, now Pat. No. 7,836,888.

(51) Int. Cl.
*A61F 5/56* (2006.01)

(52) U.S. Cl. .......... 128/848; 606/167; 606/170

(58) Field of Classification Search .......... 128/848; 606/167, 170, 174
See application file for complete search history.

(56) References Cited

U.S. PATENT DOCUMENTS

| | | | |
|---|---|---|---|
| 5,176,618 A | 1/1993 | Freedman | |
| 5,979,456 A | 11/1999 | Magovern | |
| 6,955,172 B2 | 10/2005 | Nelson et al. | |
| 7,073,505 B2 | 7/2006 | Nelson et al. | |
| 7,188,627 B2 | 3/2007 | Nelson et al. | |
| 7,216,648 B2 | 5/2007 | Nelson et al. | |
| 7,360,542 B2 | 4/2008 | Nelson et al. | |
| 7,367,340 B2 | 5/2008 | Nelson et al. | |
| 2005/0154412 A1 | 7/2005 | Krueger et al. | |
| 2005/0159637 A9 | 7/2005 | Nelson et al. | |
| 2007/0060934 A1 | 3/2007 | Rasco | |
| 2007/0102010 A1 | 5/2007 | Lemperle et al. | |
| 2007/0135803 A1 | 6/2007 | Belson | |
| 2007/0186936 A1 | 8/2007 | Nelson et al. | |
| 2007/0213733 A1 | 9/2007 | Bleich et al. | |
| 2008/0060660 A1 | 3/2008 | Nelson et al. | |
| 2008/0066764 A1 | 3/2008 | Paraschac et al. | |
| 2008/0066765 A1 | 3/2008 | Paraschac et al. | |
| 2008/0066766 A1 | 3/2008 | Paraschac et al. | |
| 2008/0066767 A1 | 3/2008 | Paraschac et al. | |

OTHER PUBLICATIONS

U.S. Appl. No. 12/072,680, filed Feb. 27, 2008, Doelling et al.

*Primary Examiner* — Patricia M Bianco
*Assistant Examiner* — Camtu T Nguyen
(74) *Attorney, Agent, or Firm* — Kilpatrick Townsend & Stockton LLP

(57) ABSTRACT

Methods and tools are disclosed for inserting an implant device that treats snoring and apnea of a patient by altering the position of a soft palate. Methods and tools can make an incision in patient's soft and hard palate to create a cavity that can house the implant. The tools can have visually observable markings that can be aligned with the incision, thus controlling the depth of the cavity. A needle having an incision edge can be used to make an incision in patient's soft palate. The needle can be bent into a suitable longitudinal shape to allow easier access and visualization of the process. A blade that makes the cavity in the tissue can be housed inside a channel in the needle. The tools may have stoppers to prevent excessive extension and retraction of the blade thus preventing an excessive cavity depth. Some tools may also house the implant device, which may be implanted after the cavity is formed.

8 Claims, 10 Drawing Sheets

DELIVERY TOOLS FOR SLEEP DISORDERS TREATMENT IMPLANT AND METHODS OF IMPLANTATION

CROSS-REFERENCES TO RELATED APPLICATIONS

This application is a continuation in part of U.S. patent applications No. 10/946,435, filed Sep. 21, 2004, now U.S. Pat. No. 7,836,888 and 11/233,493 filed Sep. 21, 2005, which are incorporated herein by reference in their entirety.

BACKGROUND OF THE INVENTION

Snoring is very common among mammals including the humans. Snoring is a noise produced while breathing during sleep due to the vibration of the soft palate and uvula. If the snoring gets worst overtime and goes untreated, it could lead to apnea.

Those with apnea stop breathing in their sleep, often hundreds of times during the night. Usually apnea occurs when the throat muscles and tongue relax during sleep and partially block the opening of the airway. When the muscles of the soft palate at the base of the tongue and the uvula relax and sag, the airway becomes blocked, making breathing difficult and noisy and even stopping it altogether. Sleep apnea also can occur in obese people when an excess amount of tissue in the airway causes a narrowing of the airway. In a given night, the number of involuntary breathing pauses or "apneic events" may be as high as 20 to 60 or more per hour. These breathing pauses are almost always accompanied by snoring between apnea episodes. Sleep apnea can also be characterized by choking sensations.

Sleep apnea is diagnosed and treated by the primary care physicians, pulmonologists, neurologists, or other physicians with specialty training in sleep disorders. Diagnosis of sleep apnea is not simple because there can be many different reasons for disturbed sleep. The specific therapy for sleep apnea is tailored to the individual patient based on medical history, physical examination, and the results of polysomnography. Medications are generally not effective in the treatment of sleep apnea. Oxygen is sometimes used in patients with central apnea caused by heart failure. It is not used to treat obstructive sleep apnea.

Nasal continuous positive airway pressure (CPAP) is the most common treatment for sleep apnea. In this procedure, the patient wears a mask over the nose during sleep, and pressure from an air blower forces air through the nasal passages. The air pressure is adjusted so that it is just enough to prevent the throat from collapsing during sleep. The pressure is constant and continuous. Nasal CPAP prevents airway closure while in use, but apnea episodes return when CPAP is stopped or it is used improperly. Many variations of CPAP devices are available and all have the same side effects such as nasal irritation and drying, facial skin irritation, abdominal bloating, mask leaks, sore eyes, and headaches. Some versions of CPAP vary the pressure to coincide with the person's breathing pattern, and other CPAPs start with low pressure, slowly increasing it to allow the person to fall asleep before the full prescribed pressure is applied.

Dental appliances that reposition the lower jaw and the tongue have been helpful to some patients with mild to moderate sleep apnea or who snore but do not have apnea. A dentist or orthodontist is often the one who fits the patient with such a device.

Some patients with sleep apnea may need surgery. Although several surgical procedures are used to increase the size of the airway, none of them is completely successful or without risks. More than one procedure may need to be tried before the patient realizes any benefits. Some of the more common procedures include removal of adenoids and tonsils (especially in children), nasal polyps or other growths, or other tissue in the airway as well as correction of structural deformities. Younger patients seem to benefit from these surgical procedures more than older patients.

Uvulopalatopharyngoplasty (UPPP) is a procedure used to remove excess tissue at the back of the throat (tonsils, uvula, and part of the soft palate). The success of this technique may range from 30 to 60 percent. The long-term side effects and benefits are not known, and it is difficult to predict which patients will do well with this procedure.

Laser-assisted uvulopalatoplasty (LAUP) is done to eliminate snoring but has not been shown to be effective in treating sleep apnea. This procedure involves using a laser device to eliminate tissue in the back of the throat. Like UPPP, LAUP may decrease or eliminate snoring but not eliminate sleep apnea itself. Elimination of snoring, the primary symptom of sleep apnea, without influencing the condition may carry the risk of delaying the diagnosis and possible treatment of sleep apnea in patients who elect to have LAUP. To identify possible underlying sleep apnea, sleep studies are usually required before LAUP is performed.

Somnoplasty is a procedure that uses RF to reduce the size of some airway structures such as the uvula and the back of the tongue. This technique helps in reducing snoring and is being investigated as a treatment for apnea.

Tracheostomy is used in persons with a severe, life-threatening sleep apnea. In this procedure, a small hole is made in the windpipe and a tube is inserted into the opening. This tube stays closed during waking hours and the person breathes and speaks normally. It is opened for sleep so that air flows directly into the lungs, bypassing any upper airway obstruction. Although this procedure is highly effective, it is an extreme measure that is rarely used.

Patients whose sleep apnea is caused by the deformities of the lower jaw may benefit from surgical reconstruction. Surgical procedures to treat obesity are sometimes recommended for sleep apnea patients who are morbidly obese. Behavioral changes are an important part of the treatment program, and in mild cases behavioral therapy may be all that is needed. Overweight persons can benefit from losing weight. Even a 10 percent weight loss can reduce the number of apneic events for most patients. Individuals with apnea should avoid the use of alcohol and sleeping pills, since they make the airway more likely to collapse during sleep and prolong the apneic periods. In some patients with mild sleep apnea, breathing pauses occur only when they sleep on their backs. In such cases, using pillows and other devices that help them sleep in a side position may be helpful.

Recently, Restore Medical, Inc., Saint Paul, Minn. has developed a new treatment for snoring and apnea, called the Pillar technique. Pillar System is a procedure where 2 or 3 small polyester rods are placed in the patient's soft palate. The Pillar System stiffens the palate thus reducing the vibration of the soft palate, and possibly prevents the airway collapse. Stiff implants in the soft palate, however, could hinder patient's normal functions like speech, ability to swallow, coughing and sneezing. Puncturing the tissue with a stiff implant is another long-term concern. Other implants have been disclosed, such as those in U.S. patent application Ser. No. 11/613,027, which is incorporated herein by reference in its. entirety.

Thus, there exists a need for methods and devices to create a cavity and to insert an implant that can treat apnea or snoring of a patient.

BRIEF SUMMARY OF THE INVENTION

The present invention relates to methods and tools for the insertion of an implant device that treats snoring and apnea of a patient by altering the position of a soft palate. The tools and methods can make an incision in patient's soft and hard palate to create a cavity that can house the implant device. A needle having an incision edge can be used to make an incision in patient's soft palate. The needle can be bent into a suitable longitudinal shape to allow easier access and visualization of the process. A blade that makes the cavity in the tissue can be housed inside a channel of the needle. The tools may have stoppers to prevent excessive extension of the blade, thus preventing an excessive cavity depth. The tools can have visually observable markings that can be aligned with the incision, thus controlling the depth of the cavity. Some tools may also house the implant device, which may be implanted after the cavity is formed.

In one embodiment, a method for treating snoring and/or apnea of a patient includes: incising a periosteum inferior to the hard palate with a cavitation tool, where the incising creates an incision, and where the cavitation tool has a needle having a posterior end, an anterior end, a channel extending the length of the needle from the posterior end of the needle to the anterior end of the needle, a blade that is adapted and configured to slide through the channel and out the posterior end of the needle, and an incising edge at the posterior end of the needle for incising the periosteum inferior to the hard palate and/or for incising the soft palate; creating a cavity within the periosteum inferior to the hard palate and within a soft palate using the cavitation tool, the creating of the cavity having the steps of entering with the needle the periosteum inferior to the hard palate through the incision created by the cavitation tool, extending the blade through the channel of the needle whereby the blade extends posterior to the posterior end of the needle, and cutting a cavity in the hard and soft palate such that the cutting comprises separating the periosteum from the hard palate and advancing the blade into the soft palate tissue; entering the cavity created within the periosteum inferior to the hard palate and the soft palate with an airway implant device loaded on an implant delivery tool that has an implant support upon which the device rests and a retractable sheath extending over at least a portion of the device and at least a portion of the implant support; and deploying the implant device into the cavity created within the periosteum inferior to the hard palate and within the soft palate, such that the deploying includes positioning the implant device within the cavity, such that the implant device is loaded on the implant delivery tool, retracting the delivery tool sheath while keeping the implant device and the implant support fixed relative to each other and in a substantially fixed position within the cavity, removing the delivery tool from the cavity, and leaving the implant device within the cavity.

In one aspect, deploying the device includes closing the incision.

In another aspect, deploying the device includes securing the airway implant device within the cavity.

In another aspect, securing the device includes suturing the device to a tissue.

In one embodiment, a cavitation tool for creating a cavity in a palate includes: a posterior end; an anterior end; a needle adapted and configured to incise and lift tissue, where the needle has a posterior end, an anterior end, and a channel extending from the posterior end of the needle to the anterior end of the needle and an incising edge at the posterior end of the needle for incising tissue; a blade having a posterior end, an anterior end, and a cutting element at the posterior end of the blade for creating a tissue cavity in which an implant may be implanted, such that the blade slides in the posterior and anterior directions within the channel of the needle and can extend out the posterior end of the needle and anterior end of the needle; a first handle connected to the needle adapted and configured to control the position of the needle; and a second handle connected to the blade at the anterior end of the blade, such that the handle is adapted and configured to slide the blade within the channel of the needle and into the tissue to create the cavity.

In another embodiment, a delivery tool for implanting an airway implant includes: a sheath; a support tube within a portion of the sheath such that the support tube and sheath are joined and such that the support tube has a cutout section; a sheath retractor joined to the support tube; an implant support within the sheath and within the support tube, such that the implant support has a posterior end, an anterior end, and a third handle fastening element aligning with the cutout section of the support tube, such that the implant support supports the implant during implantation into a cavity in the palate; and a third handle having an implant support fastening element adapted and configured to mate with the third handle fastening element, such that the third handle has a channel through which the support tube and the sheath slide anteriorly and posteriorly relative to the handle and implant support.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

DETAILED DESCRIPTION OF THE INVENTION

The embodiments of the present invention are directed toward tools and methods for inserting an implant device that treats snoring and apnea. The tools and methods can make a cavity in patient's soft and hard palate and can insert the implant device in the cavity. The tools and methods have numerous advantages. For example, the tools can have visually observable markings that can be aligned with the incision edge, thus controlling the depth of the cavity. The tools may have stoppers to prevent excessive extension and retraction of the blade. In some embodiments, the same tool may be used for the tissue cutting and implant insertion. The details of the exemplary embodiments of the present invention are explained with reference to FIGS. 1-13.

Figure 1:
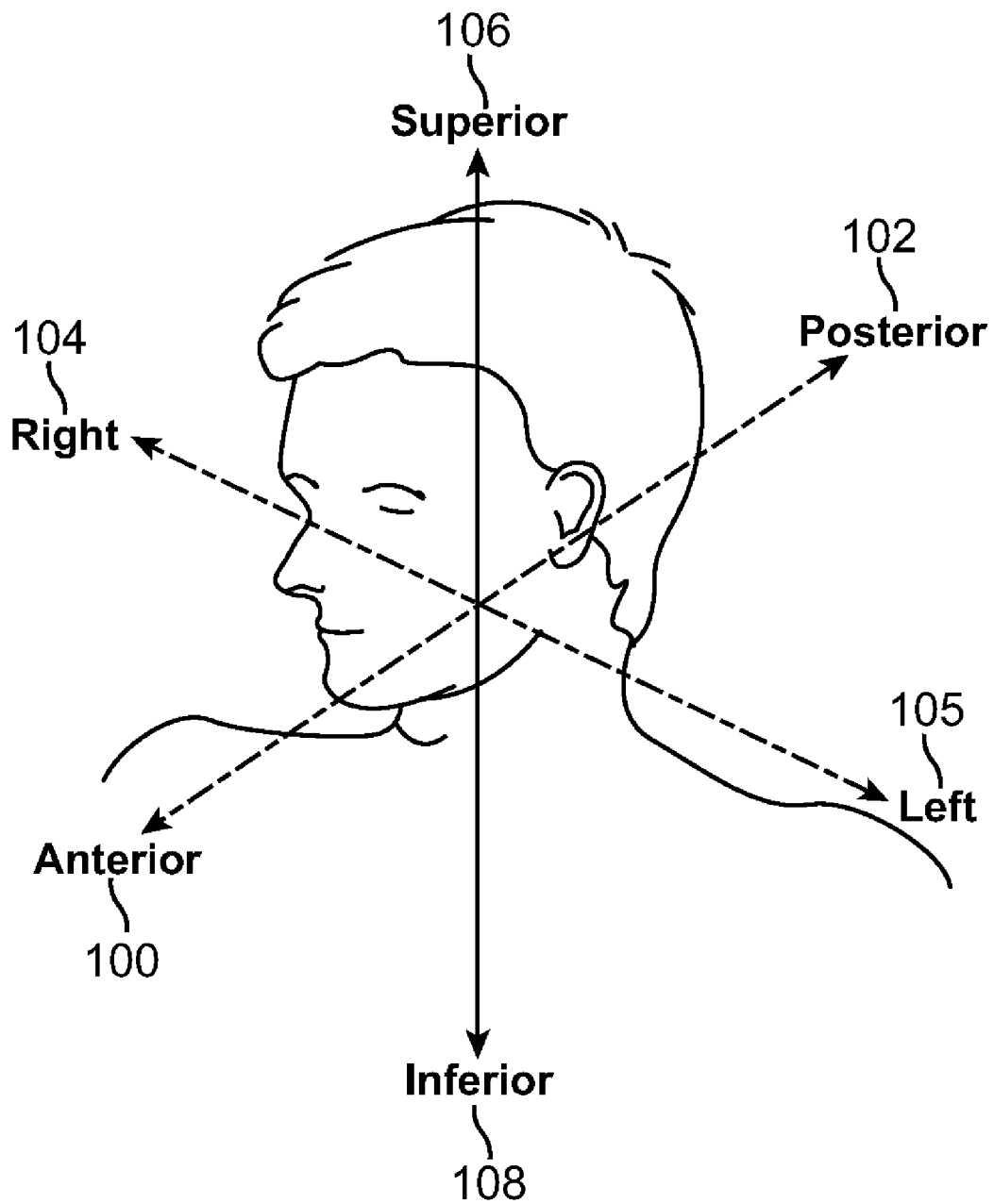
FIG. 1 illustrates the terminology used to describe object position with reference to a patient's head.

FIG. 1 illustrates the terminology used in describing position of an object with reference to the patient's head. As shown by the arrows in FIG. 1, the position of an object can be anterior or posterior, superior or inferior, and left or right. Anterior 100 refers to an area toward the front of the head or the invention, or in front of another part of the body or invention, or represents the front view of the invention. Conversely, posterior 102 refers to a part of the head or the invention toward the back of the invention or body, or behind another part of the invention or body, or represents the rear view of the body or the invention. Analog sets of definitions apply to superior 106 or inferior 108 and left 104 or right 105, as shown by the arrows in FIG. 1.

Figure 1B:
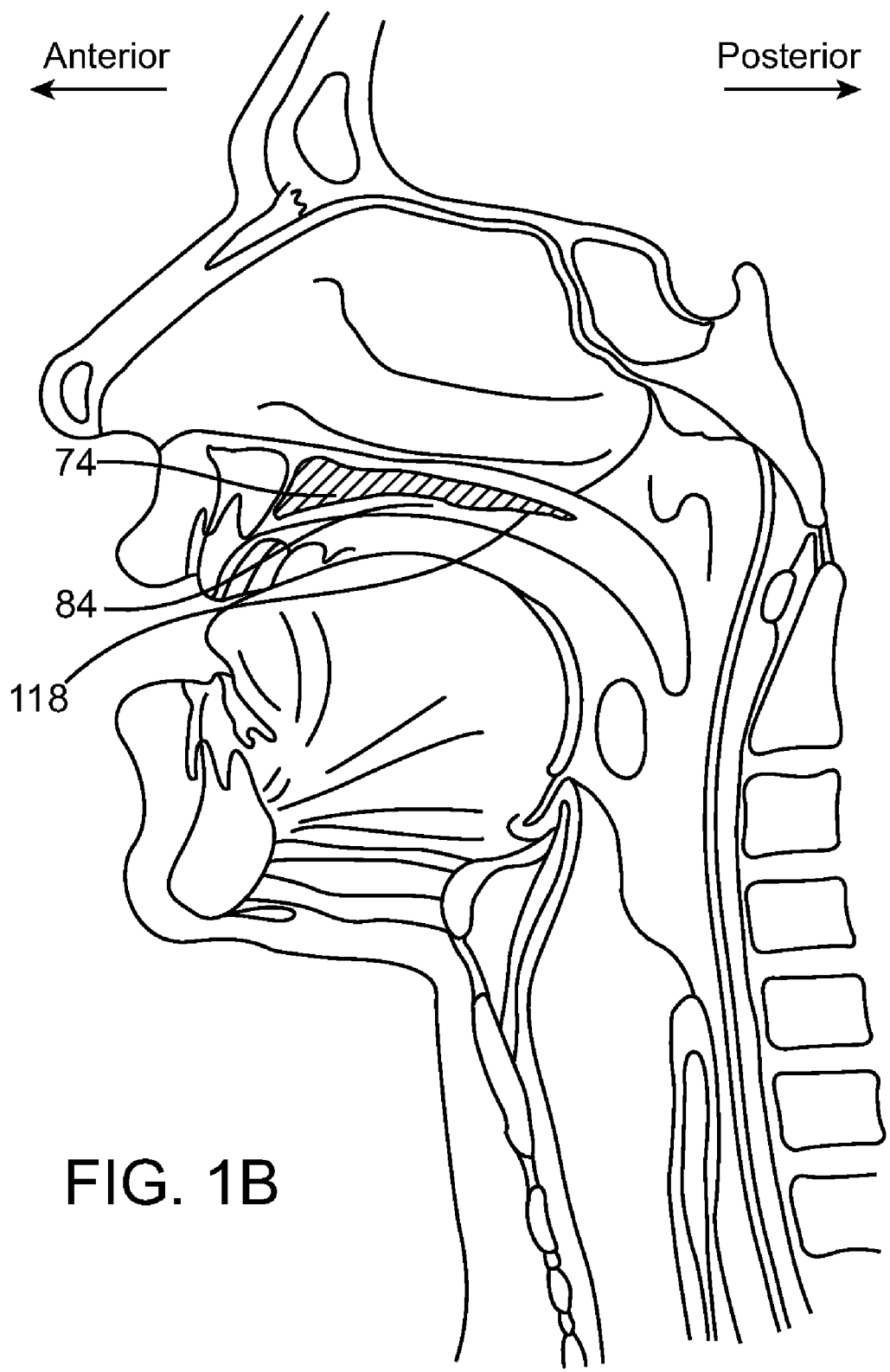
FIG. 1B is a cross sectional view of a patient's head showing the hard and soft palate.

FIG. 1B shows a cross-sectional view of patient's palate having soft palate 84 and hard palate 74. Periosteum 118 is a membrane that lines the outer surface of hard palate 74. The tools that are described below are inserted through the mouth of the patient. An incision is made in soft palate 84, and a cavity is formed in the soft palate, and may also extend to a portion of hard palate 74.

Figure 2:
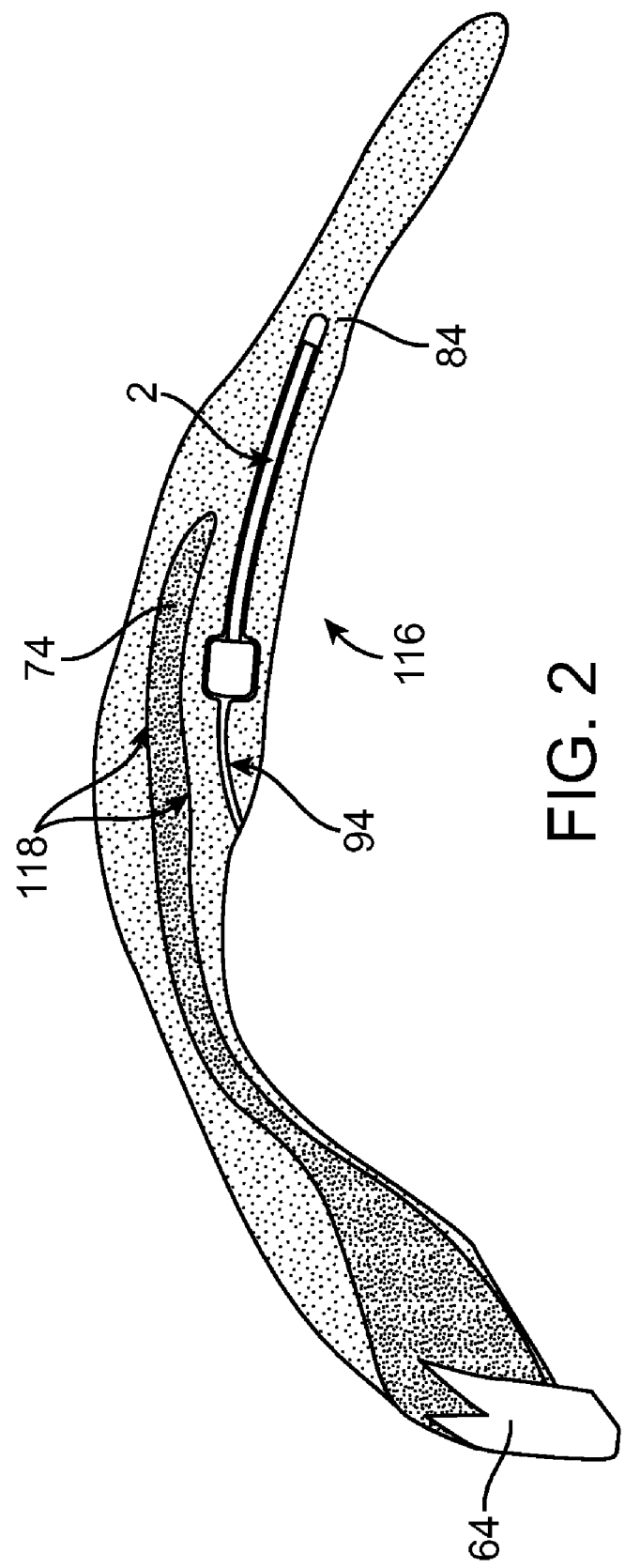
FIG. 2 illustrates an implant device in the soft palate.

FIG. 2 shows a partial cross-sectional view of a patient's mouth. Tooth 64 is on the anterior side of the mouth. Implant device 2 is inserted into cavity 94 in soft palate 84. In some embodiments of the invention, the cavity may partially extend to hard palate 74. If the cavity extends to the hard palate, then Periosteum 118 has to be separated from or lifted off hard palate 74. Implant device 2 may take different shapes and sizes. Thus, the implant device shape shown in FIG. 2 is illustrative, not restrictive.

Figure 3:
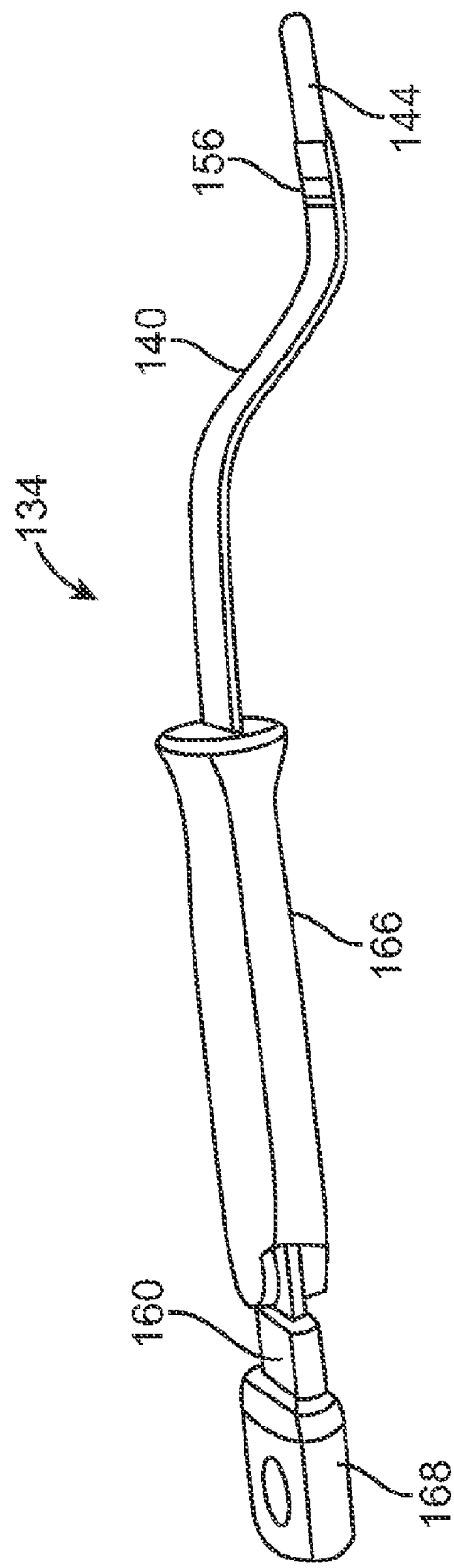
FIG. 3 is a perspective view of an embodiment of the cavitation tool.

FIG. 3 shows a perspective view of cavitation tool 134 which may be used to make incision and cavity in patient's soft and hard palate. Cavitation tool 134 has blade 144 that is partially housed in needle 140. First handle 166 can be injection molded around needle 140. A channel can extend along the interior of needle 140 thus allowing blade 144 to slide inside the needle. Blade 144 can be attached to stopper 160. The movement range of blade 144 within the channel of needle 140 can be limited by stopper 160. When the posterior end of stopper 160 and the anterior end of first handle 166 make contact, the posterior end of blade 144 extends out of needle 140 to the maximum extent. Stopper 160 can be attached to second handle 168. In some embodiments the posterior end of blade 144 may extend up to about 2.5 cm from needle 140, but other dimensions are possible depending on the required depth of the cavity. Blade 144 may be made of stainless steel, a shape memory metal (e.g. Nitinol), plastic, or other suitable material.

Needle 140 may be bent to allow easier access to the patient's palate and also to aid procedure visualization. Needle 140 can be made more rigid than blade 144, thus blade 144 having to conform to the shape of needle 140. Needle 140 can have markings 156, which may be aligned with the incision to evaluate the depth of the cavity. The needle may be made of stainless steel, a shape memory metal (e.g. Nitinol), or plastic. Other suitable materials are available.

Figure 4:
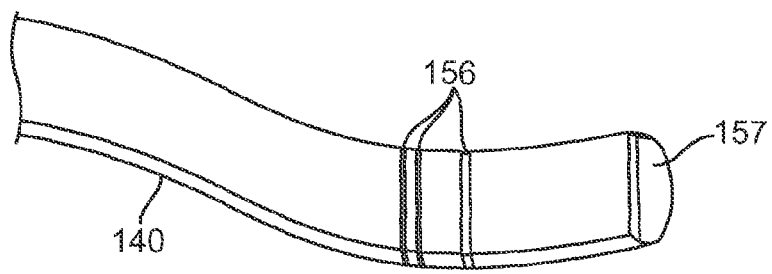
FIG. 4 is a perspective view of the distal end of a needle of the cavitation tool.

FIG. 4 shows a perspective view of the posterior end of needle 140. One or more markings 156 can be placed near the posterior side of needle 140 to help evaluate the depth of the cavity by lining the markings against the incision in soft palate 84. Markings 156 can have several lines or other indicators of the distance to the posterior tip of blade 144, thus indicating a depth of cavity 94. Markings 156 can also be used to indicate the location on patient's palate where the needle incision should be made. Needle 140 can have incising edge 157 to make an incision in the tissue, to help move the needle through the tissue, and to lift the tissue. Incising edge 157 can also be used for separating and elevating periosteum 118 from hard palate 74. Incising edge 157 can be beveled.

Figure 5:
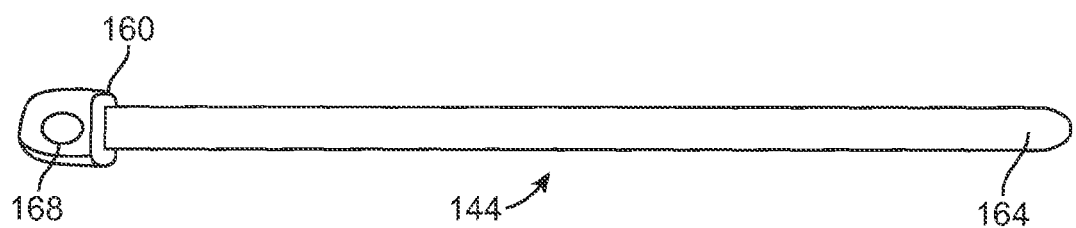
FIG. 5 is a planar view showing a blade and a second handle of the cavitation tool.

FIG. 5 shows a top planar view of blade 144 and second handle 168. Stopper 160 and second handle 168 can attach with blade 144. Stopper 160 is shown as a surface on second handle 168, but the stopper can also be a separate part. As explained in reference to FIG. 3, the location of stopper 160 determines how far first handle 166 can slide in the anterior direction relative to blade 144. Because first handle 166 is attached with needle 140, the contact between stopper 160 and first handle 166 also determines how far can blade 144 extend out of needle 140.

Figure 5A:
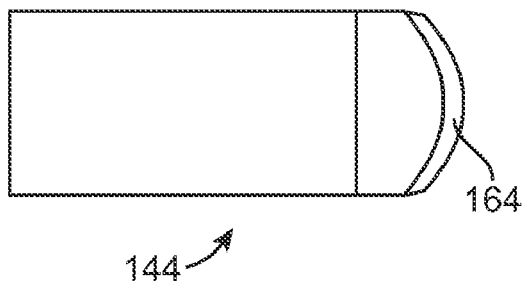
FIGS. 5A and 5B show top planar views of a rounded and an angled cutting elements of the cavitation tool blade, respectively.
Figure 5B:
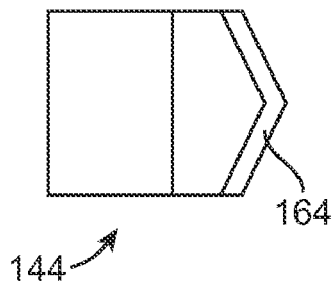

FIGS. 5A and 5B show detail views of cutting element 164 at the posterior side of blade 144. Rounded and angled cutting elements 164 are shown in FIGS. 5A and 5B, respectively. Many other shapes are possible. Cutting element 164 can be used to create a cavity in soft palate 84 and hard palate 74.

Figure 6A:
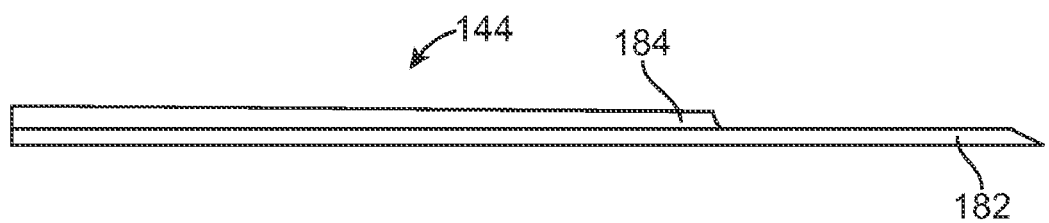
FIGS. 6A and 6B show side planar views of a blade of the cavitation tool.

FIG. 6A shows a side planar view of an embodiments of blade 144. In this embodiment, blade 144 can be configured by joining first cutting layer 182 and second layer 184. Due to smaller thickness of blade 144 at its posterior end, blade 144 is more flexible at the posterior end than at its anterior end. An increase in blade flexibility can make the blade more maneuverable.

Figure 6B:
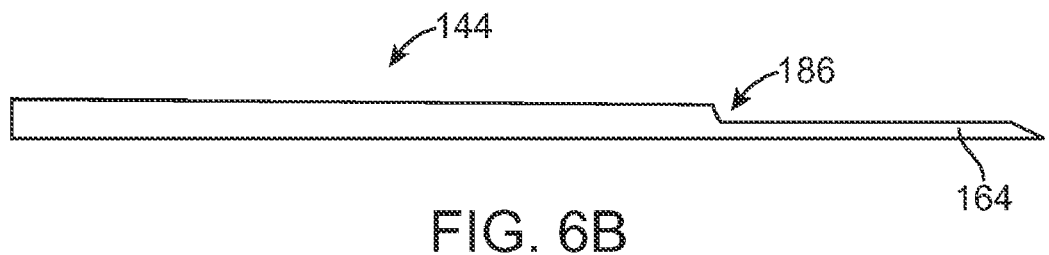

FIG. 6B shows another embodiment of blade 144 that also has variable thickness and, hence, different flexibility at its posterior and anterior ends. Blade 144 can be made of a single layer material. The posterior end of blade 144 can be tapered by grinding, chemical etching, or other processes that remove material, thus making taper 186 on the blade. The reduction of thickness of the blade 144 at its posterior end results in the increased blade flexibility at that end.

Figure 7:
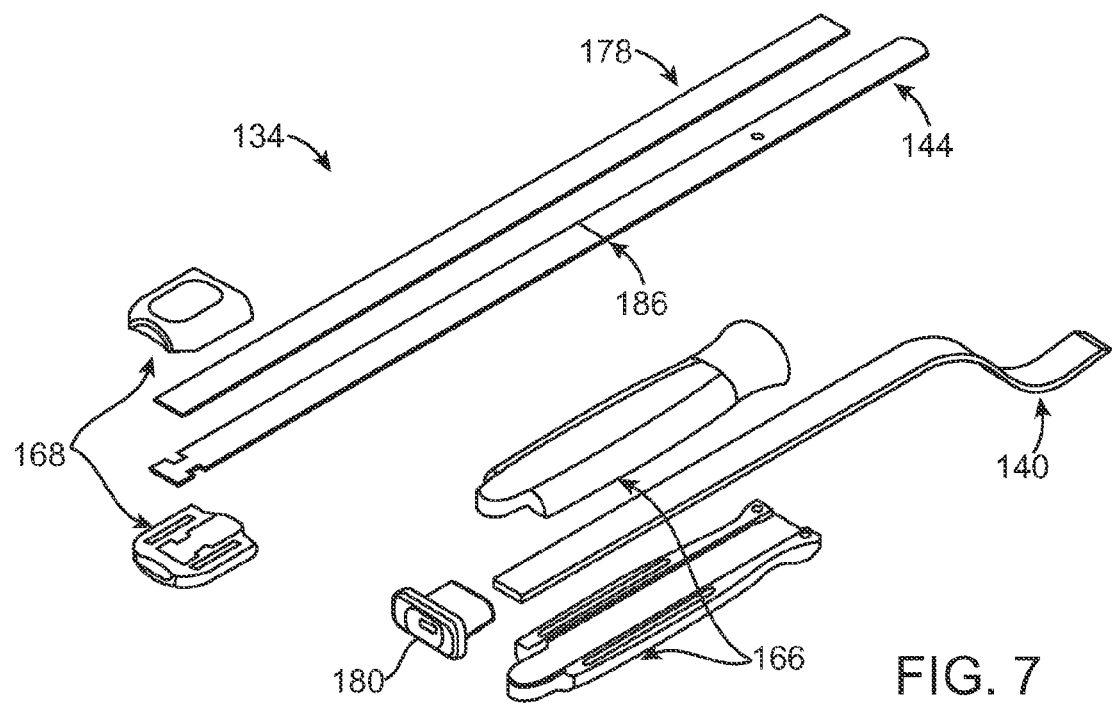
FIG. 7 is an exploded view of an embodiment of the cavitation tool.

FIG. 7 shows an exploded view of an embodiment of cavitation tool 134. In this embodiment, the external surface of blade 144 can be partially covered by heat shrink 178 from the anterior end of blade 144 to cutting element 164. Other coverage of blade 144 by heat shrink 178 is also possible. A contact between needle stopper 180 and blade stopper 160 limits the maximum extension of the posterior end of blade 144 relative to the posterior end of needle 140. The cavitation tool can be sterilized.

Figure 8:
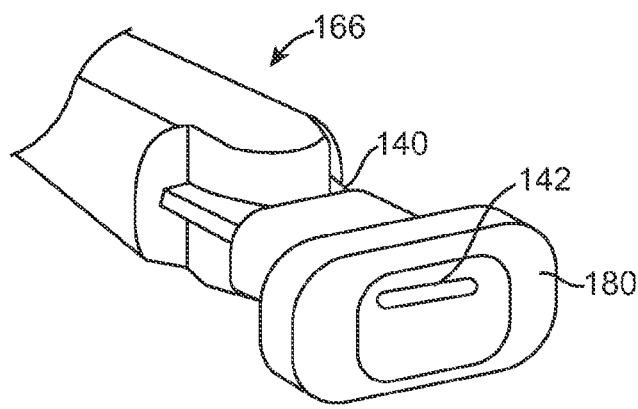
FIG. 8 is a partial view of the anterior end of the needle and needle stopper of the cavitation tool.

FIG. 8 shows the anterior end of needle 140 and needle stopper 180 in an embodiment of the cavitation tool. Needle 140 can extend through first handle 166 and needle stopper 180, ending at the anterior end of needle stopper 180. Needle 140 can have needle channel 142 that can house blade 144.

Figure 9:
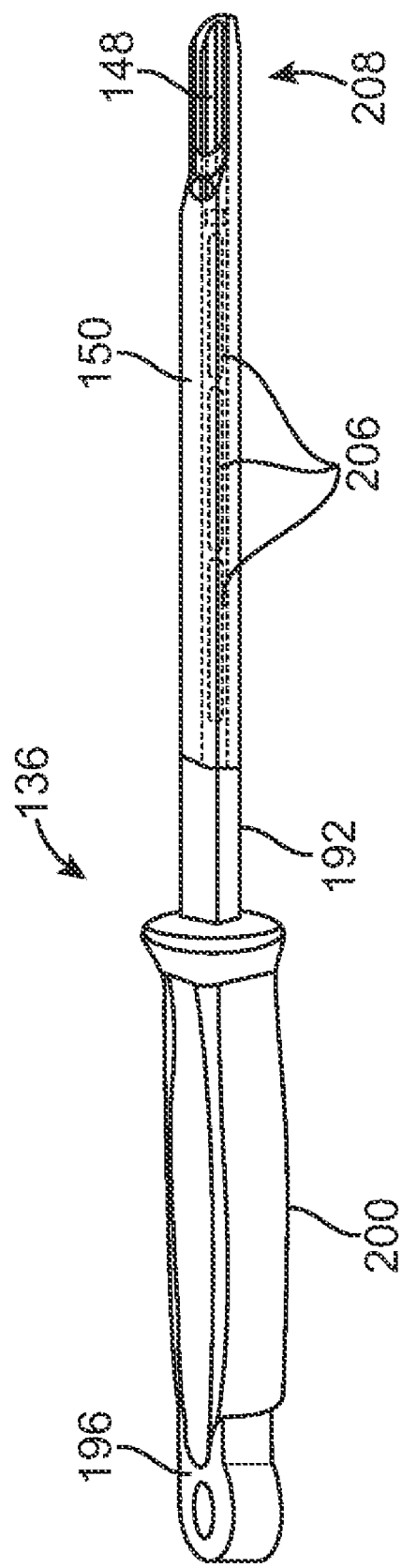
FIG. 9 shows an isometric view of an embodiment of an implant delivery tool.

FIG. 9 shows an isometric view of one embodiment of delivery tool 136. Implant device 2 (not shown) can be supported by implant support 148 and covered by sheath 150. Delivery tool 136 can be used for deploying the implant into the cavity. The implant device can be loaded on the delivery tool and deployed into the cavity by advancing the posterior end of the delivery tool into the cavity, followed by retracting sheath 150 towards the anterior end of the delivery tool while keeping the delivery tool in a substantially fixed position within the cavity. Implant device 2, which is covered by sheath 150 at the posterior end of the delivery tool, can thus be freed from the contact with sheath 150, and left in the cavity. Sheath 150 can be clear or translucent to visually aid the deployment of the implant device. After deploying the implant device in the cavity and removing the delivery tool, the incision can be closed by, for example, suturing or other methods. The deployed implant device can be secured in the cavity by, for example, adhering the device to the tissue using a tissue adhesive, or by suturing the device to the tissue, or by other methods.

Figure 10:
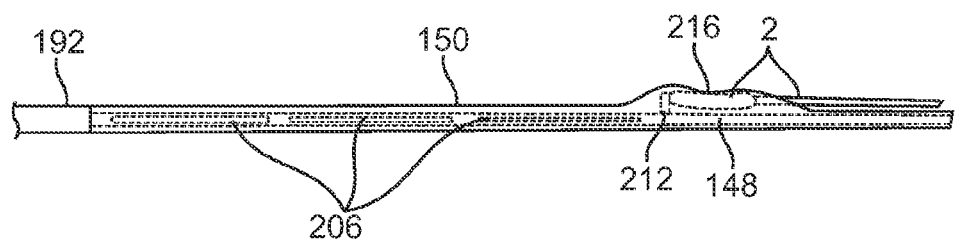
FIG. 10 shows a partial cross-sectional view of an embodiment of the implant delivery tool.

FIG. 10 shows a partial side view of implant device 2, implant support 148, sheath 150, and support tube 192. Implant device 2 can be held in place by implant support 148 and sheath 150. The anterior end of implant device 2 can be in contact with abutting portion 212 on implant support 148. Abutting portion 212 can be made by joining with implant support 148, but it can also be made by, for example, stamping a suitable portion of implant support 148 in the superior direction, thus creating a flap against which implant device 2 can abut. Thus, implant device 2 can be partially or fully supported on its inferior and anterior ends by implant support 148 and abutting portion 212, respectively. Implant support 148 may be made of stainless steel, a shape memory metal (e.g. Nitinol), plastic, or other suitable material. Furthermore, implant device 2 can be partially supported on its left and right ends by sheath 150. The superior end of implant device 2 can also be supported by sheath 150 which may have dimple 216 to hold the implant device in place.

Figure 11:
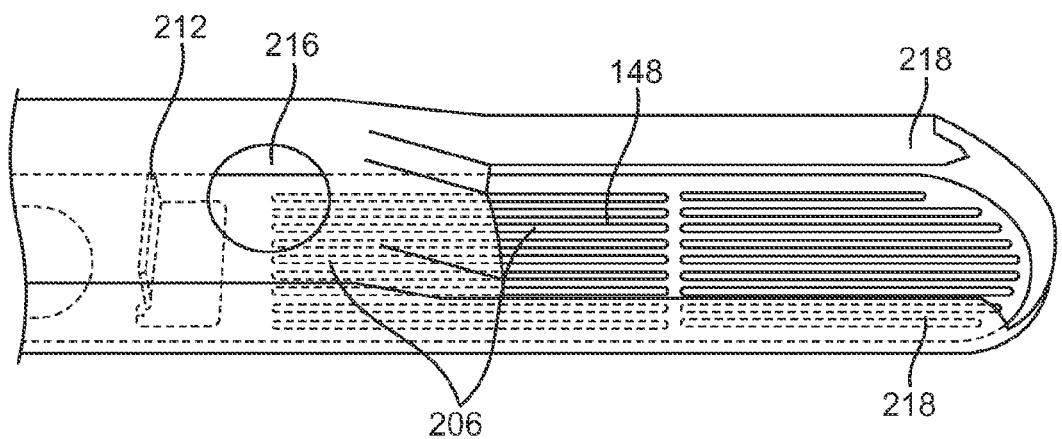
FIG. 11 shows an isometric view of the posterior end of an embodiment of the implant delivery tool.

Support for implant device 2 is illustrated in FIG. 11 which shows an isometric view of the posterior end of one embodiment of the delivery tool. Implant support 148 supports the inferior side of implant device 2 (not shown). Implant support 148 can have cutout section 206 with one or more cutouts which make implant support 148 more flexible, hence easier to maneuver. Cutout section 206 shown in FIG. 11 has the cutouts that are smaller in the vicinity of the posterior side of the implant support, and larger away from the posterior side, but other arrangements are also possible. An embodiment of abutting portion 212 that is a flap is shown, but other types of abutting portion 212 are also possible, for example an abutting portion that is joined with implant support 148. Sheath 150 has sheath flaps 218 to support the left and right lateral ends of the implant device. Dimple 216 can be configured to align the implant device on implant support 148 by pressing against the superior side of the implant device.

Figure 12:
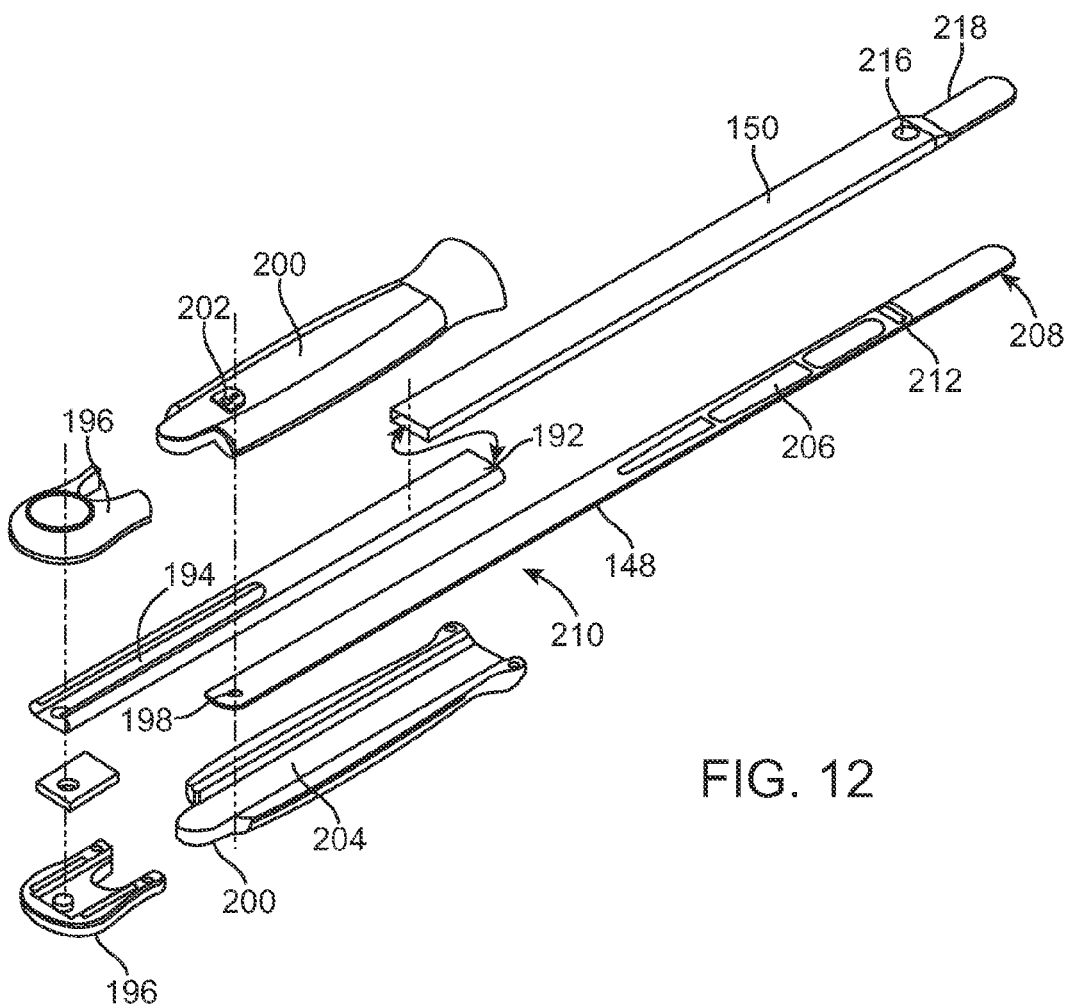
FIG. 12 shows an exploded view of an embodiment of the implant delivery tool.

FIG. 12 shows an exploded view of one embodiment of implant delivery tool 136. The anterior end of sheath 150 and the posterior end of support tube 192 can be joined. Sheath retractor 196 can be attached with the anterior end of support tube 192. Therefore, a movement of sheath retractor 196 in the anterior direction causes support tube 192 to move in the same direction, which, in turn, causes sheath 150 to follow, too. The retraction of sheath 150 along implant support 148 does not cause implant device 2 to move in the anterior direction because abutting portion 212 prevents implant device 2 from sliding along implant support 148.

Implant support 148 can slide inside sheath 150 and support tube 192. Implant support 148 can attach with third handle 200 using fastening element 202 which is positioned on the superior side of third handle 200. The superior and inferior sections of third handle 200 can be connected on their outside edges thus forming third handle channel 204 through the interior of third handle 200. Support tube 192 and sheath 150 can slide inside third handle channel 204. Thus, in the embodiment shown in FIG. 12, implant support 148 can slide inside support tube 192 and sheath 150, which, in turn, can slide inside third handle channel 204. When support tube 192 and sheath 150 slide inside third handle channel 204, the range of their anterior-posterior motion is limited by the length of cutout section 194 on the superior side of support tube 192, because the sliding stops when the posterior end of cutout section 194 reaches fastening element 202 on third handle 200. The range of anterior-posterior motion for support tube 192 and sheath 150 can be selected such that implant device 2 is secured when sheath 150 is in its posterior position and is released when sheath 150 is moved to the anterior position. The implant delivery tool can be sterilized.

Figure 13:
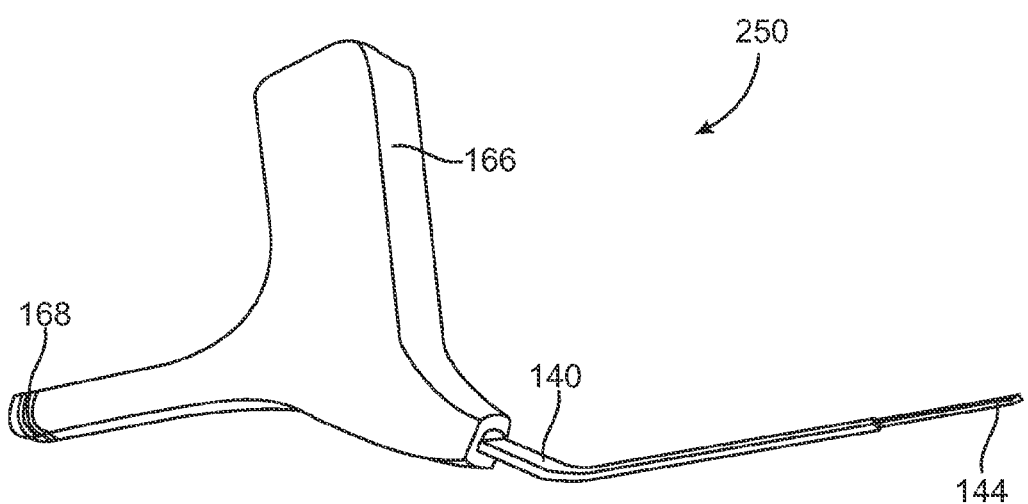
FIG. 13 illustrates an embodiment of a combined delivery and cavitation tool.

FIG. 13 illustrates an embodiment of combined cavitation and delivery tool 250. The combined cavitation and delivery tool can have first handle 166 connected to and controlling the position of needle 140, second handle 168 connected to blade 144, and a delivery element for delivering the implant into the cavity created by the tool.

As will be understood by those skilled in the art, the present invention may be embodied in other specific forms without departing from the essential characteristics thereof. For example, the lateral support for the implant device may be provided by the implant support, and not by the sheath. Also, a needle may take many different longitudinal shapes, including a straight needle. The implant delivery tool may be used to deliver medications or diagnostic instruments or similar to the cavity. Many other embodiments are possible without deviating from the spirit and scope of the invention. These other embodiments are intended to be included within the scope of the present invention, which is set forth in the following claims.

What is claimed is:

1. A method for treating snoring and/or apnea of a patient comprising the steps of:
    incising a periosteum inferior to the hard palate with a cavitation tool, wherein the incising creates an incision, and wherein the cavitation tool comprises a needle comprising a posterior end, an anterior end, a channel extending the length of the needle from the posterior end of the needle to the anterior end of the needle, a blade wherein the blade is adapted and configured to slide through the channel and out the posterior end of the needle, and an incising edge at the posterior end of the needle for incising the periosteum inferior to the hard palate and/or for incising the soft palate;
    creating a cavity within the periosteum inferior to the hard palate and within a soft palate using the cavitation tool, the creating of the cavity comprising
    entering with the needle the periosteum inferior to the hard palate through the incision created by the cavitation tool,
    extending the blade through the channel of the needle wherein the blade extends posterior to the posterior end of the needle, and
    cutting a cavity in the hard and soft palate wherein the cutting comprises separating the periosteum from the hard palate and advancing the blade into the soft palate tissue;
    entering the cavity created within the periosteum inferior to the hard palate and the soft palate with an implant device loaded on an implant delivery tool, the implant delivery tool comprising an implant support upon which the device rests and a retractable sheath extending over at least a portion of the device and at least a portion of the implant support; and deploying the implant device into the cavity created within the periosteum inferior to the hard palate and within the soft palate, whereby the deploying comprises positioning the implant device within the cavity, wherein the implant device is loaded on the implant delivery tool, retracting the delivery tool sheath while keeping the implant device and the implant support fixed relative to each other and in a substantially fixed position within the cavity, removing the delivery tool from the cavity, and leaving the implant device within the cavity.

2. The method of claim 1 further comprising a step chosen from a group consisting of closing the incision, securing the implant device within the cavity, or a combination thereof.

3. The method of claim 2 wherein the step of securing is chosen from a group consisting of suturing the device to a tissue, adhering the device to a tissue using a tissue adhesive, or a combination thereof.

4. The method of claim 1 wherein the cavitation tool and the delivery tool are part of a single unit.

5. The method of claim 1 wherein the step of entering the periosteum includes approximately aligning a marking on the needle with the incision created by the cavitation tool.

6. The method of claim 5 wherein the step of extending the blade includes limiting the blade from extending more than a distance from the marking of the needle.

7. The method of claim 6 wherein the step of limiting the blade posterior motion includes using a relative configuration of the blade and needle to create an cavity appropriately sized for the implant device, wherein the relative configuration of the blade and needle results from the blade comprising a stopper at an anterior end of the blade wherein the stopper prevents the blade from extending out the posterior end of the needle more than a distance from a marking on the needle.

8. The method of claim 7 wherein the distance is approximately 2.5 centimeters.

\* \* \* \* \*